US008426382B2

(12) United States Patent
Soula et al.

(10) Patent No.: US 8,426,382 B2
(45) Date of Patent: Apr. 23, 2013

(54) POLYSACCHARIDES COMPRISING CARBOXYL FUNCTIONAL GROUPS SUBSTITUTED BY A HYDROPHOBIC ALCOHOL DERIVATIVE

(75) Inventors: Remi Soula, Lyons (FR); Olivier Soula, Meyzieu (FR); Gerard Soula, Meyzieu (FR); Richard Charvet, Rillieux la Pape (FR)

(73) Assignee: Adocia, Lyons (FR)

( * ) Notice: Subject to any disclaimer, the term of this patent is extended or adjusted under 35 U.S.C. 154(b) by 253 days.

(21) Appl. No.: 12/662,184

(22) Filed: Apr. 5, 2010

(65) Prior Publication Data
US 2010/0305035 A1 Dec. 2, 2010

Related U.S. Application Data

(63) Continuation-in-part of application No. 12/588,149, filed on Oct. 6, 2009, now abandoned.

(60) Provisional application No. 61/136,816, filed on Oct. 6, 2008.

(30) Foreign Application Priority Data

Oct. 6, 2008 (FR) ..................... 08 05506

(51) Int. Cl.
*A01N 43/04* (2006.01)
*A01N 61/00* (2006.01)
*A61K 31/715* (2006.01)
*A61K 31/00* (2006.01)

(52) U.S. Cl.
USPC ................ 514/54; 514/59; 514/57; 514/1

(58) Field of Classification Search .......... 514/54, 514/57, 59, 1
See application file for complete search history.

(56) References Cited

U.S. PATENT DOCUMENTS

| 4,826,818 | A | 5/1989 | Mori et al. |
| 2002/0143160 | A1 | 10/2002 | Sunamoto et al. |
| 2008/0234227 | A1 | 9/2008 | Soula et al. |
| 2009/0221805 | A1* | 9/2009 | Dahri-Correia et al. ...... 530/399 |

FOREIGN PATENT DOCUMENTS

| DE | 41 36 324 A1 | 5/1993 |
| EP | 0 160 103 B1 | 6/1990 |
| EP | 0 609 968 A2 | 8/1994 |
| EP | 0 831 143 A1 | 3/1998 |
| EP | 1 222 926 A1 | 7/2002 |
| FR | 2 914 305 B1 | 7/2009 |
| JP | A-61-069801 | 4/1986 |
| JP | A-03-292301 | 12/1991 |
| WO | WO 2007/034320 A2 * | 3/2007 |
| WO | WO 2008/038111 A1 | 4/2008 |

OTHER PUBLICATIONS

Ando, H.Y. and Radebaugh, G.W. (2000) "Preformulation" in Remington: The Science and Practice of Pharmacy, 20th Edition. Edited by Alfonso R. Gennaro. p. 704-712.*
Written Opinion of the International Searching Authority dated Jun. 9, 2011 in International Application No. PCT/IB2009/007054.
Pelletier et al., "Amphiphilic derivatives of sodium alginate and hyaluronate: synthesis and physico-chemical properties of aqueous dilute solutions," *Carbohydrate Polymers*, vol. 43, pp. 343-349, 2000.
Miralles-Houzelle et al., Hydrophobic Alkyl Chains-Pectin Conjugates. Comparative Study of Some Physicochemical Properties in Relation to Covalent Coupling vs Ionic Association, *Langmuir*, vol. 17, pp. 1384-1391, 2001.
Nichifor et al., "Bile acids covalently bound to polysaccharides I. Esters of bile acids with dextran," *European Polymer Journal*, vol. 35, pp. 2125-2129, 1999.
Akiyama et al., "Self-Assembled Nanogels of Cholesteryl-Modified Polysaccharides: Effect of the Polysaccharide Structure on Their Association Characteristics in the Dilute and Semidilute Regimes," *Biomacromolecules*, vol. 8, pp. 2366-2373, 2007.
Heinze et al., "Functional Polymers Based on Dextran," *Adv. Polym. Sci.*, vol. 205, pp. 199-291, 2006.
Sánchez-Chaves et al., "Poly (vinyl alcohol) functionalized by monosuccinate groups. Coupling of bioactive amino compounds," *Polymer*, vol. 39, No. 13, pp. 2751-2757, 1998.
Takata et al., "Prodrugs of Vitamin E. 1. Preparation and Enzymatic Hydrolysis of Aminoalkanecarboxylic Acid Esters of d-α-Tocopherol," *Journal of Pharmaceutical Sciences*, vol. 84, No. 1, pp. 96-100, 1995.
Ma et al., "Evaluation of blood circulation of polysaccharide surface-decorated PLA nanoparticles," *Carbohydrate Polymers*, vol. 72, pp. 75-81, 2008.
Yinsong et al., "Preparation and characterization of self-aggregated nanoparticles of cholesterol-modified O-carboxymethyl chitosan conjugates," *Carbohydrate Polymers*, vol. 69, pp. 597-606, 2007.

(Continued)

*Primary Examiner* — Scarlett Goon
(74) *Attorney, Agent, or Firm* — Oliff & Berridge, PLC

(57) ABSTRACT

The invention relates to a polysaccharide comprising carboxyl functional groups, one at least of which is substituted by a derivative of a hydrophobic alcohol. The invention also relates to a pharmaceutical composition comprising one of the polysaccharides according to the invention and at least one active principle. It also relates to a pharmaceutical composition, wherein the active principle is chosen from the group consisting of proteins, glycoproteins, peptides and nonpeptide therapeutic molecules. The invention also relates to the use of the functionalized polysaccharides according to the invention in the preparation of pharmaceutical compositions as described above.

26 Claims, No Drawings

OTHER PUBLICATIONS

Nishikawa et al., "Macromolecular Complexation between Bovine Serum Albumin and the Self-Assembled Hydrogel Nanoparticle of Hydrophobized Polysaccharides," *J. Am. Chem. Soc.*, vol. 118, pp. 6110-6115, 1996.

Taniguchi et al., "Self-aggregate nanoparticles of cholesteryl and galactoside groups-substituted pullulan and their specific binding to galactose specific lectin, $RCA_{120}$", *Macromol. Chem. Phys.*, vol. 200, pp. 1554-1560, 1999.

Search Report dated May 20, 2009 issued in French Patent Application No. 0805506 (with translation).

International Search Report dated Dec. 10, 2009 issued in International Application No. PCT/IB2009/007054.

McKarns et al., "Correlation Between Hydrophobicity of Short-Chain Aliphatic Alcohols and Their Ability to Alter Plasma Membrane Integrity", Fundamental and Applied Toxicology, 36, 62-70 (1997).

Material Safety Data Sheet for Methanol, Sigma-Aldrich (2012).
Material Safety Data Sheet for Ethanol, Sigma-Aldrich (2012).
Material Safety Data Sheet for 2-Propanol, Sigma-Aldrich (2012).

\* cited by examiner

POLYSACCHARIDES COMPRISING CARBOXYL FUNCTIONAL GROUPS SUBSTITUTED BY A HYDROPHOBIC ALCOHOL DERIVATIVE

The present invention relates to novel biocompatible polymers based on polysaccharides comprising carboxyl functional groups which can be of use, in particular for the administration of active principle(s) (AP(s)) to man or animals with a therapeutic and/or prophylactic purpose.

Hydrophobic alcohols are of advantage in the formulation of pharmaceutical active principles, in particular because of their biocompatibility and their hydrophobic nature, which makes it possible to adjust the hydrophobicity of the polymers to which they may be grafted.

Their biocompatibility is excellent insofar as they play a role in many biochemical processes and are present in the esterified form in the majority of tissues.

However, it is known to a person skilled in the art that it is difficult to graft an alcohol to a polysaccharide comprising carboxyl functional groups since it is difficult to be selective between the hydroxyl functions of the polysaccharide and the hydroxyl function of the hydrophobic alcohol. During grafting, the alcohols of the polymer may compete with the alcohol of the graft, if it is not desired to have recourse to techniques for the protection/deprotection of the alcohols of the polymer, and this side reaction results in the crosslinking of the polymer chains. Thus, advantageous hydrophobic alcohols, such as cholesterol, could not to date be grafted to polysaccharides comprising carboxyl functional groups.

Dellacherie et al. have developed esters of polysaccharides, i.e. of alginates, of hyaluronates (Pelletier, S. et al., Carbohydr. Polym., 2000, 43, 343-349) or of galacturonans (Dellacherie, Edith et al., Langmuir, 2001, 17, 1384-1391), by a synthetic method employing alkyl α-halides, bromododecane and bromooctadecane. The synthesis of the esters consists in substituting the halides by tetrabutylammonium carboxylates. This method makes it possible to access esters of hydrophobic alcohols but it is limited to halogenated alkyl derivatives which can undergo nucleophilic substitution. It thus cannot be employed to graft hydrophobic alcohols such as cholesterol. Furthermore, these halogenated derivatives exhibit risks of toxicity and are thus not safe to use in the development of a pharmaceutical product.

Other researchers have got round this difficulty by grafting hydrophobic acids instead of hydrophobic alcohols. Nichifor et al., for example, have employed cholic acid, a steroid derivative, in order to graft it directly to dextran alcohols (Nichifor, Marieta et al., Eur. Polym. J., 1999, 35, 2125-2129). This method gets round the problem of cholesterol by employing a derivative exhibiting a carboxylic acid capable of reacting with the alcohols of a polysaccharide. However, cholic acid is not approved by the FDA for injections, in contrast to cholesterol, and this strategy cannot be employed with polysaccharides comprising carboxyl functional groups.

Other researchers have employed nonanionic polysaccharides in order to be able to graft hydrophobic alcohols. Akiyoshi et al., for example, have converted cholesterol, which is nucleophilic, to an electrophilic derivative (Biomacromolecules, 2007, 8, 2366-2373). This electrophilic derivative of cholesterol could be grafted to the alcohol functions of pullulan or mannan, which are neutral polysaccharides. Again, this strategy cannot be employed with polysaccharides comprising carboxyl functional groups.

A recent review of functional dextran-based polymers (Heinze, Thomas et al., Adv. Polym. Sci., 2006, 205, 199-291) reports modifications by hydrophobic acids, inter alia, but does not report dextran functionalized by hydrophobic alcohols.

The present invention relates to novel derivatives of amphiphilic polysaccharides comprising carboxyl functional groups partially substituted by at least one hydrophobic alcohol derivative. These novel derivatives of polysaccharides comprising carboxyl functional groups have a good biocompatibility and their hydrophobicity can be easily adjusted without detrimentally affecting the biocompatibility.

It also relates to a synthetic method which makes it possible to solve the abovementioned synthesis problems. This method has made it possible to obtain polysaccharides comprising carboxyl functional groups partially substituted by hydrophobic alcohols, including, for example, cholesterol.

The invention thus relates to polysaccharides comprising carboxyl functional groups, one at least of which is substituted by a derivative of a hydrophobic alcohol, denoted HA:

said hydrophobic alcohol (HA) being grafted or bonded to the anionic polysaccharide via a coupling arm R, said coupling arm being bonded to the anionic polysaccharide via a function F, said function F resulting from the coupling between the amine function of the connecting arm R and a carboxyl function of the anionic polysaccharide, and said coupling arm being bonded to the hydrophobic alcohol via a function G resulting from the coupling between a carboxyl, isocyanate, thioacid or alcohol function of the coupling arm and a functional group of the hydrophobic alcohol, the unsubstituted carboxyl functions of the anionic polysaccharide being in the cationic carboxylate form, the cation preferably being that of an alkali metal, such as $Na^+$ or $K^+$, F being an amide function, G being either an ester, thioester, carbonate or carbamate function, R being a chain comprising between 1 and 18 carbons which is optionally branched and/or unsaturated, which optionally comprises one or more heteroatoms, such as O, N and/or S, and which has at least one acid function, HA being a residue of a hydrophobic alcohol, the product of the coupling between the hydroxyl function of the hydrophobic alcohol and at least one electrophilic function carried by the group R, said polysaccharide comprising carboxyl functional groups being amphiphilic at neutral pH.

In one embodiment, G is an ester function.

According to the invention, the polysaccharide comprising carboxyl functional groups partially substituted by hydrophobic alcohols is chosen from the polysaccharides comprising carboxyl functional groups of general formula I:

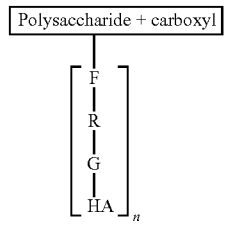

formula I in which n represents the molar fraction of the carboxyl functions of the polysaccharide substituted by F-R-G-HA and is between 0.01 and 0.7, F, R, G and HA corresponding to the definitions given above, and, when the carboxyl function of the polysaccharide is not substituted by F-R-G-HA, then the carboxyl functional group or groups of the polysaccharide are cation carboxylates, the cation preferably being that of an alkali metal, such as $Na^+$ or $K^+$.

In one embodiment, the polysaccharides comprising carboxyl functional groups are polysaccharides naturally carrying carboxyl functional groups and are chosen from the group consisting of alginate, hyaluronan and galacturonan.

In one embodiment, the polysaccharides comprising carboxyl functional groups are synthetic polysaccharides obtained from polysaccharides naturally comprising carboxyl functional groups or from neutral polysaccharides, to which at least 15 carboxyl functional groups per 100 saccharide units have been grafted, of general formula II:

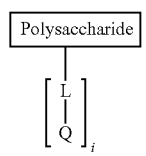

II the natural polysaccharides being chosen from the group of polysaccharides predominantly composed of glycoside monomers bonded via glycoside bonds of (1,6) and/or (1,4) and/or (1,3) and/or (1,2) type, L being a bond resulting from the coupling between the connecting arm Q and an —OH function of the polysaccharide and being either an ester, thioester, carbonate, carbamate or ether function, i representing the molar fraction of the L-Q substituents per saccharide unit of the polysaccharide, Q being a chain comprising between 1 and 18 carbons which is optionally branched and/or unsaturated, which comprises one or more heteroatoms, such as O, N and/or S, and which comprises at least one carboxyl functional group —$CO_2H$.

In one embodiment, n is between 0.05 and 0.5.

In one embodiment, the polysaccharide is predominantly composed of glycoside monomers bonded via glycoside bonds of (1,6) type.

In one embodiment, the polysaccharide predominantly composed of glycoside monomers bonded via glycoside bonds of (1,6) type is dextran.

In one embodiment, the polysaccharide is predominantly composed of glycoside monomers bonded via glycoside bonds of (1,4) type.

In one embodiment, the polysaccharide predominantly composed of glycoside monomers bonded via glycoside bonds of (1,4) type is chosen from the group consisting of pullulan, alginate, hyaluronan, xylan, galacturonan and a water-soluble cellulose.

In one embodiment, the polysaccharide is a pullulan.
In one embodiment, the polysaccharide is an alginate.
In one embodiment, the polysaccharide is a hyaluronan.
In one embodiment, the polysaccharide is a xylan.
In one embodiment, the polysaccharide is a galacturonan.
In one embodiment, the polysaccharide is a water-soluble cellulose.

In one embodiment, the polysaccharide is predominantly composed of glycoside monomers bonded via glycoside bonds of (1,3) type.

In one embodiment, the polysaccharide predominantly composed of glycoside monomers bonded via glycoside bonds of (1,3) type is a curdlan.

In one embodiment, the polysaccharide is predominantly composed of glycoside monomers bonded via glycoside bonds of (1,2) type.

In one embodiment, the polysaccharide predominantly composed of glycoside monomers bonded via glycoside bonds of (1,2) type is an inulin.

In one embodiment, the polysaccharide is predominantly composed of glycoside monomers bonded via glycoside bonds of (1,4) and (1,3) type.

In one embodiment, the polysaccharide predominantly composed of glycoside monomers bonded via glycoside bonds of (1,4) and (1,3) type is a glucan.

In one embodiment, the polysaccharide is predominantly composed of glycoside monomers bonded via glycoside bonds of (1,4) and (1,3) and (1,2) type.

In one embodiment, the polysaccharide predominantly composed of glycoside monomers bonded via glycoside bonds of (1,4) and (1,3) and (1,2) type is mannan.

In one embodiment, the polysaccharide according to the invention is characterized in that the group Q is chosen from the following groups:

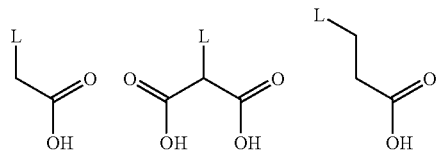

In one embodiment, i is between 0.1 and 2.
In one embodiment, i is between 0.2 and 1.5.

In one embodiment, the group R according to the invention is noteworthy in that it is chosen from amino acids.

In one embodiment, the amino acids are chosen from α-amino acids.

In one embodiment, the α-amino acids are chosen from natural α-amino acids.

In one embodiment, the natural α-amino acids are chosen from leucine, alanine, isoleucine, glycine, phenylalanine, tryptophan or valine.

In one embodiment, the hydrophobic alcohol is chosen from fatty alcohols.

In one embodiment, the hydrophobic alcohol is chosen from the alcohols composed of a saturated or unsaturated and branched or unbranched alkyl chain comprising from 4 to 18 carbons.

In one embodiment, the hydrophobic alcohol is chosen from the alcohols composed of a saturated or unsaturated and branched or unbranched alkyl chain comprising from 6 to 18 carbons.

In one embodiment, the hydrophobic alcohol is chosen from the alcohols composed of a saturated or unsaturated and branched or unbranched alkyl chain comprising from 8 to 16 carbons.

In one embodiment, the hydrophobic alcohol is octanol.
In one embodiment, the hydrophobic alcohol is 2-ethylbutanol.

In one embodiment, the fatty alcohol is chosen from myristyl alcohol, cetyl alcohol, stearyl alcohol, cetearyl alcohol, butyl alcohol, oleyl alcohol or lanolin.

In one embodiment, the hydrophobic alcohol is chosen from cholesterol derivatives.

In one embodiment, the cholesterol derivative is cholesterol.

In one embodiment, the hydrophobic alcohol is chosen from menthol derivatives.

In one embodiment, the hydrophobic alcohol is menthol in its racemic form.

In one embodiment, the hydrophobic alcohol is the D isomer of menthol.

In one embodiment, the hydrophobic alcohol is the L isomer of menthol.

In one embodiment, the hydrophobic alcohol is chosen from tocopherols.

In one embodiment, the tocopherol is $\alpha$-tocopherol.

In one embodiment, the $\alpha$-tocopherol is the racemate of $\alpha$-tocopherol.

In one embodiment, the tocopherol is the D isomer of $\alpha$-tocopherol.

In one embodiment, the tocopherol is the L isomer of $\alpha$-tocopherol.

In one embodiment, the hydrophobic alcohol is chosen from alcohols carrying an aryl group.

In one embodiment, the alcohol carrying an aryl group is chosen from benzyl alcohol or phenethyl alcohol.

The polysaccharide can have a degree of polymerization m of between 10 and 10 000.

In one embodiment, it has a degree of polymerization m of between 10 and 1000.

In another embodiment, it has a degree of polymerization m of between 10 and 500.

The invention also relates to the synthesis of the polysaccharides comprising partially substituted carboxyl functional groups according to the invention.

Said synthesis comprises a step of obtaining an amino intermediate HA-G-R—$NH_2$ or an ammonium salt HA-G-R—$NH_3^+$, the counterion of which is an anion chosen from halides, sulfates, sulfonates or carboxylates, and a step of grafting this amino intermediate to a carboxyl function of a polysaccharide, R, G and HA corresponding to the definitions given above.

In one embodiment, a step of functionalizing the polysaccharide with at least 15 carboxyl functional groups per 100 saccharide units is carried out by grafting compounds of formula Q-L', L' being an anhydride, halide, carboxylic acid, thioacid or isocyanate function, to at least 15 alcohol functions per 100 saccharide units of the polysaccharide, Q and L corresponding to the definitions given above.

In one embodiment, the amino intermediate of formula HA-G-R—$NH_2$ or HA-G-R—$NH_3^+$ is obtained by reaction of a compound of formula G'-R—$NH_2$, G' being a carboxylic acid, isocyanate, thioacid or alcohol function, with the alcohol function of the hydrophobic alcohol, R, G and HA corresponding to the definitions given above.

If necessary, in this step of obtaining the amino intermediate, use is made of the protection/deprotection techniques well known to a person skilled in the art of peptide synthesis.

Preferably, the step of grafting the amino intermediate to an acid function of the polysaccharide is carried out in an organic medium.

The invention also relates to the use of the functionalized polysaccharides according to the invention in the preparation of pharmaceutical compositions as described above.

The invention also relates to a pharmaceutical composition comprising one of the polysaccharides according to the invention as described above and at least one active principle.

The invention also relates to a pharmaceutical composition according to the invention as described above, wherein the active principle is chosen from the group consisting of proteins, glycoproteins, peptides and nonpeptide therapeutic molecules.

Active principle is understood to mean a product in the form of a single chemical entity or in the form of a combination having a physiological activity. Said active principle can be exogenous, that is to say that it is introduced by the composition according to the invention. It can also be endogenous, for example the growth factors which will be secreted in a wound during the first phase of healing and which can be retained on said wound by the composition according to the invention.

Depending on the pathologies targeted, it is intended for a local or systemic treatment.

In the case of local and systemic releases, the methods of administration envisaged are by the intravenous, subcutaneous, intradermal, transdermal, intramuscular, oral, nasal, vaginal, ocular, buccal or pulmonary route, and the like.

The pharmaceutical compositions according to the invention are either in the liquid form, in aqueous solution, or in the powder, implant or film form. They additionally comprise the conventional pharmaceutical excipients well known to a person skilled in the art.

Depending on the pathologies and methods of administration, the pharmaceutical compositions can advantageously comprise, in addition, excipients which make it possible to formulate them in the form of a gel, sponge, injectable solution, solution to be taken orally, lyophilized tablet, and the like.

The invention also relates to a pharmaceutical composition according to the invention as described above, which can be administered in the form of a stent, of a film or coating of implantable biomaterials, or of an implant.

EXAMPLE 1

Synthesis of Sodium Dextranmethylcarboxylate Modified by Cholesterol Leucinate

Cholesterol leucinate, para-toluenesulfonic acid salt, is obtained according to the process described in the patent (Kenji, M et al., U.S. Pat. No. 4,826,818).

8 g (i.e. 148 mmol of hydroxyl functions) of dextran with a weight-average molar mass of approximately 40 kg/mol (Fluka) are dissolved in water at 42 g/l. 15 ml of 10N NaOH (148 mmol of NaOH) are added to this solution. The mixture is brought to 35° C. and then 23 g (198 mmol) of sodium chloroacetate are added. The temperature of the reaction medium is brought to 60° C. at 0.5° C./min and then maintained at 60° C. for 100 minutes. The reaction medium is diluted with 200 ml of water, neutralized with acetic acid and purified by ultrafiltration through a 5 kD PES membrane against 6 volumes of water. The final solution is quantitatively determined by dry extract, in order to determine the concentration of polymer, and then quantitatively determined by acid/base titration in 50/50 (v/v) water/acetone, in order to determine the degree of substitution with methylcarboxylates.

According to the dry extract: [polymer]=31.5 mg/g

According to the acid/base titration: the degree of substitution of the hydroxyl functions by methylcarboxylate functions is 1.04 per saccharide unit.

The sodium dextranmethylcarboxylate solution is passed over a Purolite resin (anionic) in order to obtain the dextranmethylcarboxylic acid, which is subsequently lyophilized for 18 hours.

8 g of dextranmethylcarboxylic acid (37 mmol of methylcarboxylic acid functions) are dissolved in DMF at 45 g/l and then cooled to 0° C. 0.73 g of cholesterol leucinate, para-toluenesulfonic acid salt (1 mmol) is suspended in DMF at 100 g/l. 0.11 g of triethylamine (1 mmol) is subsequently added to this suspension. Once the polymer solution is at 0° C., 0.109 g (1 mmol) of NMM and 0.117 g (1 mmol) of EtOCOCl are subsequently added. After reaction for 10 min, the cholesterol leucinate suspension is added. The medium is subsequently maintained at 4° C. for 15 minutes. The medium is subsequently heated to 30° C. Once at 30° C., the medium is subsequently run into a 5 g/l solution of 3.76 g of NMM (37 mmol) with vigorous stirring. The solution is ultrafiltered through a 10 kD PES membrane against 10 volumes of 0.9% NaCl solution and then 5 volumes of water. The concentration of the polymer solution is determined by dry extract. A fraction of solution is lyophilized and analyzed by $^1$H NMR in $D_2O$ in order to determine the level of acid functions converted to cholesterol leucinate amide.

According to the dry extract: [modified polymer]=12.9 mg/g

According to the $^1$H NMR: the molar fraction of the acids modified by the cholesterol leucinate per saccharide unit is 0.03.

EXAMPLE 2

Synthesis of Sodium Dextransuccinate Modified by Cholesterol Leucinate

Cholesterol leucinate, para-toluenesulfonic acid salt, is obtained according to the process described in the patent (Kenji, M et al., U.S. Pat. No. 4,826,818).

Sodium dextransuccinate is obtained from dextran 40 according to the method described in the paper by Sanchez-Chaves et al. (Sanchez-Chaves, Manuel et al., Polymer, 1998, 39 (13), 2751-2757). The level of acid functional groups per glycoside unit (i) is 1.46, according to the $^1$H NMR in $D_2O$/NaOD.

The sodium dextransuccinate solution is passed over a Purolite resin (anionic) in order to obtain dextransuccinic acid, which is subsequently lyophilized for 18 hours.

7.1 g of dextransuccinic acid (23 mmol) are dissolved in DMF at 44 g/l. The solution is cooled to 0° C. 0.77 g of cholesterol leucinate, para-toluenesulfonic acid salt (1 mmol) is suspended in DMF at 100 g/l. 0.12 g of triethylamine (TEA) (1 mmol) is subsequently added to this suspension. Once the polymer solution is at 0° C., 0.116 g (1 mmol) of NMM and 0.124 g (1 mmol) of EtOCOCl are subsequently added. After reacting for 10 min, the cholesterol leucinate suspension is added. The medium is subsequently maintained at 4° C. for 15 minutes. The medium is subsequently heated to 30° C. Once at 30° C., the medium is subsequently run into a 5 g/l solution of 3.39 g of NMM (33 mmol) with vigorous stirring. The solution is ultrafiltered through a 10 kD PES membrane against 10 volumes of 0.9% NaCl solution and then 5 volumes of water. The concentration of the polymer solution is determined by dry extract. A fraction of solution is lyophilized and analyzed by $^1$H NMR in $D_2O$ in order to determine the level of acid functions converted to cholesterol leucinate amide.

According to the dry extract: [modified polymer]=17.5 mg/g

According to the $^1$H NMR: the molar fraction of the acids modified by the cholesterol leucinate per saccharide unit is 0.05.

EXAMPLE 3

Synthesis of Sodium Pullulansuccinate Modified by Cholesterol Leucinate

Cholesterol leucinate, para-toluenesulfonic acid salt, is obtained according to the process described in the patent (Kenji, M et al., U.S. Pat. No. 4,826,818).

10 g of pullulan with a weight-average molar mass of approximately 100 kg/mol (Fluka) are dissolved in DMSO at a concentration of 400 mg/g at 60° C. This solution is equilibrated at 40° C. and then two DMF solutions comprising 9.27 g of succinic anhydride (371 g/l) and 9.37 g of NMM (375 g/l) are added to the pullulan solution. The reaction time is 240 min, starting from the addition of the NMM solution. The solution thus obtained is diluted in 1 l of water and ultrafiltered through a 10 kD PES membrane against a 0.9% sodium chloride solution and then against double distilled water. The concentration of sodium pullulansuccinate in the final solution is determined by dry extract and the dry product is analyzed by $^1$H NMR in $D_2O$/NaOD in order to determine the level of hydroxyl functions converted to succinic ester per saccharide unit.

According to the dry extract: [pullulansuccinate]=15.8 mg/g

According to the $^1$H NMR: the molar fraction of the alcohols carrying a sodium succinate per saccharide unit is 1.35.

The sodium pullulansuccinate solution is acidified on a Purolite resin (anionic) and is then subsequently lyophilized for 18 hours.

5 g of pullulansuccinic acid are dissolved in DMF at 51 g/l. The solution is cooled to 0° C. 0.08 g of NMM and 0.08 g of EtOCOCl are subsequently added. After reacting for 10 min, a suspension comprising 0.51 g of cholesterol leucinate, para-toluenesulfonic acid (PTSA) salt, and 0.08 g of TEA in 5.1 ml of DMF is added. The grafting time is 20 min, after the introduction of the cholesterol derivative. The medium is subsequently heated to 30° C. and then run into an aqueous NMM solution (2.09 g at 5 mg/ml). The solution obtained is diluted by adding 100 ml of water and then diafiltered through a 10 kD PES membrane against a 0.9% sodium chloride solution and then against double distilled water. The concentration of sodium pullulansuccinate modified by the cholesterol leucinate in the final solution is determined by dry extract and the dry product is analyzed by $^1$H NMR in $D_2O$/NaOD in order to determine the level of acid functions converted to cholesterol leucinate amide.

According to the dry extract: [modified polymer]=2.9 mg/g

According to the NMR: the molar fraction of the acids modified by the cholesterol leucinate per saccharide unit is 0.04.

EXAMPLE 4

Synthesis of Sodium Pullulansuccinate Modified by the Alaninate of Cetyl Alcohol The alaninate of cetyl alcohol is obtained according to the process described in the patent (Kenji, M et al., U.S. Pat. No. 4,826,818).

A sodium pullulansuccinate solution obtained as described in example 3 is acidified on a Purolite resin (anionic) and is then subsequently lyophilized for 18 hours.

5 g of pullulansuccinic acid are dissolved in DMF at 51 g/l. The solution is cooled to 0° C. 0.32 g of NMM (3.2 mmol) and 0.32 g of EtOCOCl (3.2 mmol) are subsequently added. After reacting for 10 min, a suspension comprising 1.55 g of alaninate of cetyl alcohol, para-toluenesulfonic acid salt (3.2 mmol) and 0.32 g of TEA (3.2 mmol) in 20.4 ml of DMF is added. The grafting time is 20 min, after the introduction of the cetyl alcohol derivative. The medium is subsequently heated to 30° C. and then run into an aqueous NMM solution (8.36 g at 5 mg/ml). The solution obtained is diluted by adding 100 ml of water and then diafiltered through a 10 kD PES membrane against a 0.9% sodium chloride solution and then against double distilled water. The concentration of sodium pullulansuccinate modified by the alaninate of cetyl alcohol in the final solution is determined by dry extract and the dry product is analyzed by $^1$H NMR in $D_2O$/NaOD in order to determine the level of acid functions converted to amide of alaninate of cetyl alcohol.

According to the dry extract: [modified polymer]=5.2 mg/g

According to the NMR: the molar fraction of the acids modified by alaninate of cetyl alcohol per saccharide unit is 0.18.

EXAMPLE 5

Synthesis of Sodium Dextranmethylcarboxylate Modified by Dodecanol Alaninate

Dodecanol alaninate, para-toluenesulfonic acid salt, is obtained according to the process described in the patent (Kenji, M et al., U.S. Pat. No. 4,826,818).

A sodium dextranmethylcarboxylate solution obtained as described in example 1 is passed over a Purolite resin (anionic) in order to obtain dextranmethylcarboxylic acid, which is subsequently lyophilized for 18 hours.

5 g of dextranmethylcarboxylic acid (23.2 mmol of methylcarboxylic acid functions) are dissolved in DMF at 45 g/l and then cooled to 0° C. 1.99 g of dodecanol alaninate, para-toluenesulfonic acid salt (4.6 mmol) are suspended in DMF at 100 g/l. 0.47 g of triethylamine (4.6 mmol) is subsequently added to this suspension. Once the polymer solution is at 0° C., 2.35 g (23.2 mmol) of NMM and 2.52 g (23.2 mmol) of EtOCOCl are subsequently added. After reacting for 10 min, the dodecanol alaninate suspension is added. The medium is subsequently maintained at 4° C. for 15 minutes. The medium is subsequently heated to 30° C. Once at 30° C., an imidazole solution (3.2 g in 9.3 ml of water) is added to the reaction medium. The polymer solution is ultrafiltered through a 10 kD PES membrane against 10 volumes of 0.9% NaCl solution and then 5 volumes of water. The concentration of the polymer solution is determined by dry extract. A fraction of solution is lyophilized and analyzed by $^1$H NMR in $D_2O$ in order to determine the level of acid functions modified by dodecanol alaninate.

According to the dry extract: [modified polymer]=22 mg/g

According to the $^1$H NMR: the molar fraction of the acids modified by the dodecanol alaninate per saccharide unit is 0.19.

EXAMPLE 6

Synthesis of Sodium Dextranmethylcarboxylate Modified by L-Menthol Glycinate

L-Menthol glycinate, para-toluenesulfonic acid salt, is obtained according to the process described in the patent (Kenji, M et al., U.S. Pat. No. 4,826,818).

As the oil obtained comprises impurities, the amine salt is neutralized by a stoichiometric addition of sodium hydroxide and extracted with diisopropyl ether. The organic phase is then acidified with a solution of HCl in ethyl ether and the HCl salt of the menthol derivative is extracted with water. After lyophilization, L-menthol glycinate, hydrochloric acid salt, is obtained.

A sodium dextranmethylcarboxylate solution obtained as described in example 1 is passed over a Purolite resin (anionic) in order to obtain dextranmethylcarboxylic acid, which is subsequently lyophilized for 18 hours.

12 g of dextranmethylcarboxylic acid (59.22 mmol of methylcarboxylic acid functions) are dissolved in DMF at 60 g/l and then cooled to 0° C. 1.32 g of L-menthol glycinate, hydrochloric acid salt (5.29 mmol) are suspended in DMF at 100 g/l. 0.54 g of triethylamine (5.29 mmol) is subsequently added to this suspension. Once the polymer solution is at 0° C., a solution of NMM (6.59 g, 65.1 mmol) in DMF (530 g/l) and 7.07 g (65.1 mmol) of EtOCOCl are subsequently added. After reacting for 10 minutes, the L-menthol glycinate suspension is added. The medium is subsequently maintained at 10° C. for 45 minutes. The medium is subsequently heated to 50° C. An imidazole solution (14.7 g in 22 ml of water) and 65 ml of water are added to the reaction medium. The polymer solution is ultrafiltered through a 10 kD PES membrane against 6 volumes of 0.9% NaCl solution, 4 volumes of 0.01N sodium hydroxide solution, 7 volumes of 0.9% NaCl solution and then 3 volumes of water. The concentration of the polymer solution is determined by dry extract. A fraction of solution is lyophilized and analyzed by $^1$H NMR in $D_2O$ in order to determine the level of acid functions converted to L-menthol glycinate amide.

According to the dry extract: [modified polymer]=25.7 mg/g

According to the $^1$H NMR: the molar fraction of the acids modified by the L-menthol glycinate per saccharide unit is 0.09.

EXAMPLE 7

Synthesis of Sodium Dextranmethylcarboxylate Modified by (±)-α-Tocopherol Alaninate (±)-α-Tocopherol alaninate, hydrochloric acid salt, is obtained according to the process described in J. Pharm. Sci., 1995, 84(1), 96-100.

A sodium dextranmethylcarboxylate modified by (±)-α-tocopherol alaninate is obtained by a process similar to that described in example 6.

According to the dry extract: [modified polymer]=28.1 mg/g

According to the $^1$H NMR: the molar fraction of the acids modified by the (±)-α-tocopherol alaninate per saccharide unit is 0.04.

EXAMPLE 8

Synthesis of Sodium Dextranmethylcarboxylate Modified by Octanol Glycinate

Octanol glycinate, para-toluenesulfonic acid salt, is obtained according to the process described in the patent (Kenji, M et al., U.S. Pat. No. 4,826,818).

A sodium dextranmethylcarboxylate modified by octanol glycinate is obtained by a process similar to that described in example 6.

According to the dry extract: [modified polymer]=34.1 mg/g

According to the $^1$H NMR: the molar fraction of the acids modified by the octanol glycinate per saccharide unit is 0.27.

EXAMPLE 9

Synthesis of Sodium Dextranmethylcarboxylate Modified by Dodecanol Glycinate

Dodecanol glycinate, para-toluenesulfonic acid salt, is obtained according to the process described in the patent (Kenji, M et al., U.S. Pat. No. 4,826,818).

A sodium dextranmethylcarboxylate modified by dodecanol glycinate is obtained by a process similar to that described in example 6.

According to the dry extract: [modified polymer]=25.3 mg/g

According to the $^1$H NMR: the molar fraction of the acids modified by the dodecanol glycinate per saccharide unit is 0.1.

EXAMPLE 10

Synthesis of Sodium Dextranmethylcarboxylate Modified by Dodecanol Glycinate (Dextran 10 kDa)

A sodium dextranmethylcarboxylate, synthesized according to the process described in example 1 using a dextran with a weight-average molecular weight of approximately 10 kg/mol (Pharmacosmos), modified by dodecanol glycinate is obtained by a process similar to that described in example 9.

According to the dry extract: [modified polymer]=23.6 mg/g

According to the $^1$H NMR: the molar fraction of the acids modified by the dodecanol glycinate per saccharide unit is 0.09.

EXAMPLE 11

Synthesis of Sodium Dextranmethylcarboxylate Modified by Tetradecanol Glycinate

Tetradecanol glycinate, para-toluenesulfonic acid salt, is obtained according to the process described in the patent (Kenji, M et al., U.S. Pat. No. 4,826,818).

The sodium dextranmethylcarboxylate is synthesized according to the process described in example 1 using a dextran with a weight-average molecular weight of approximately 10 kg/mol (Pharmacosmos).

A sodium dextranmethylcarboxylate modified by tetradecanol glycinate is obtained by a process similar to that described in example 6.

According to the dry extract: [modified polymer]=22.9 mg/g

According to the $^1$H NMR: the molar fraction of the acids modified by the tetradecanol glycinate per saccharide unit is 0.09.

EXAMPLE 12

Synthesis of Sodium Dextranmethylcarboxylate Modified by the Glycinate of Cetyl Alcohol The glycinate of cetyl alcohol, para-toluenesulfonic acid salt, is obtained according to the process described in the patent (Kenji, M et al., U.S. Pat. No. 4,826,818).

The sodium dextranmethylcarboxylate is synthesized according to the process described in example 1 using a dextran with a weight-average molecular weight of approximately 10 kg/mol (Pharmacosmos).

A sodium dextranmethylcarboxylate modified by the glycinate of cetyl alcohol is obtained by a process similar to that described in example 6.

According to the dry extract: [modified polymer]=19 mg/g

According to the $^1$H NMR: the molar fraction of the acids modified by the glycinate of cetyl alcohol per saccharide unit is 0.05.

EXAMPLE 13

Synthesis of Sodium Dextranmethylcarboxylate Modified by Octanol Phenylalaninate Octanol phenylalaninate, para-toluenesulfonic acid salt, is obtained according to the process described in the patent (Kenji, M et al., U.S. Pat. No. 4,826,818).

A sodium dextranmethylcarboxylate modified by octanol phenylalaninate is obtained by a process similar to that described in example 6.

According to the dry extract: [modified polymer]=30.2 mg/g

According to the $^1$H NMR: the molar fraction of the acids modified by octanol phenyl phenylalaninate per saccharide unit is 0.09.

EXAMPLE 14

Synthesis of Sodium Dextranmethylcarboxylate Modified by 3,7-dimethyl-1-octanol Phenylalaninate 3,7-dimethyl-1-octanol phenylalaninate, para-toluenesulfonic acid salt, is obtained according to the process described in the patent (Kenji, M et al., U.S. Pat. No. 4,826,818).

A sodium dextranmethylcarboxylate modified by 3,7-dimethyl-1-octanol phenylalaninate is obtained by a process similar to that described in example 6.

According to the dry extract: [modified polymer]=29 mg/g

According to the $^1$H NMR: the molar fraction of the acids modified by the 3,7-dimethyl-1-octanol phenylalaninate per saccharide unit is 0.1.

EXAMPLE 15

Synthesis of Sodium Dextranmethylcarboxylate Modified by Citronellol Phenylalaninate Citronellol phenylalaninate, para-toluenesulfonic acid salt, is obtained according to the process described in the patent (Kenji, M et al., U.S. Pat. No. 4,826,818).

A sodium dextranmethylcarboxylate modified by citronellol phenylalaninate is obtained by a process similar to that described in example 6.

According to the dry extract: [modified polymer]=28.1 mg/g

According to the $^1$H NMR: the molar fraction of the acids modified by the citronellol phenylalaninate per saccharide unit is 0.1.

EXAMPLE 16

Synthesis of Sodium Dextranmethylcarboxylate Modified by Decanol Phenylalaninate Decanol phenylalaninate, para-toluenesulfonic acid salt, is obtained according to the process described in the patent (Kenji, M et al., U.S. Pat. No. 4,826,818).

A sodium dextranmethylcarboxylate modified by decanol phenylalaninate is obtained by a process similar to that described in example 6.

According to the dry extract: [modified polymer]=25 mg/g

According to the $^1$H NMR: the molar fraction of the acids modified by the decanol phenylalaninate per saccharide unit is 0.1.

EXAMPLE 17

Synthesis of Sodium Dextranmethylcarboxylate Modified by Dodecanol Phenylalaninate Dodecanol phenylalaninate, para-toluenesulfonic acid salt, is obtained according to the process described in the patent (Kenji, M et al., U.S. Pat. No. 4,826,818).

A sodium dextranmethylcarboxylate modified by dodecanol phenylalaninate is obtained by a process similar to that described in example 6.

According to the dry extract: [modified polymer]=20 mg/g

According to the $^1$H NMR: the molar fraction of the acids modified by the dodecanol phenylalaninate per saccharide unit is 0.1.

EXAMPLE 18

Synthesis of Sodium Dextranmethylcarboxylate Modified by the Phenylalaninate of Benzyl Alcohol A sodium dextranmethylcarboxylate modified by the phenylalaninate of benzyl alcohol is obtained, by a process similar to that described in example 6, using the phenylalaninate of benzyl alcohol, hydrochloric acid salt (Bachem).

According to the dry extract: [modified polymer]=47.7 mg/g

According to the $^1$H NMR: the molar fraction of the acids modified by the phenylalaninate of benzyl alcohol per saccharide unit is 0.41.

EXAMPLE 19

Synthesis of Sodium Dextranmethylcarboxylate Modified by Isohexanol Phenylalaninate Isohexanol phenylalaninate, para-toluenesulfonic acid salt, is obtained according to the process described in the patent (Kenji, M et al., U.S. Pat. No. 4,826,818).

A sodium dextranmethylcarboxylate modified by isohexanol phenylalaninate is obtained by a process similar to that described in example 6.

According to the dry extract: [modified polymer]=29.8 mg/g

According to the $^1$H NMR: the molar fraction of the acids modified by the isohexanol phenylalaninate per saccharide unit is 0.18.

EXAMPLE 20

Dissolution of a BMP-2 lyophilizate

A test of dissolution of a Bone Morphogenetic Protein 2 (BMP-2) lyophilizate was developed in order to demonstrate the solubilizing power of different polymers as a physiological pH. The BMP-2 is dissolved in a buffer comprising sucrose (Sigma), glycine (Sigma), glutamic acid (Sigma), sodium chloride (Riedel-de-Haën) and polysorbate 80 (Fluka). The pH of this solution is adjusted to pH 4.5 by addition of sodium hydroxide and then the solution is lyophilized. 283.2 mg of lyophilizate comprise approximately 12 mg of BMP-2.

The polymers according to the invention are employed in this test. Sodium dextranmethylcarboxylate modified by ethyl phenylalaninate, a polymer described in patent application FR0702316, is also employed in this test by way of comparison.

The test consists in introducing approximately exactly 4 mg of lyophilizate comprising 0.168 mg of BMP-2. The lyophilizate is subsequently taken up in 210 µl of an aqueous solution in order to achieve a final concentration of BMP-2 to 0.8 mg/ml as a physiological pH, the final concentration of polymer being 5 mg/ml.

The visual appearance of the solution is recorded after stirring for 5 minutes at a low speed on a roll.

The results for different solutions are collated in the following table.

| Solution | Visual appearance | pH |
|---|---|---|
| Water | clear | 4.3 |
| Example 13 | clear | 7.4 |
| Example 8 | clear | 7.5 |
| Example 5 | clear | 7.4 |
| Counterexample FR0702316 | cloudy | 7.5 |

The addition of water results in a clear BMP-2 solution but at an acidic pH.

This test makes it possible to demonstrate the improvement in the dissolution of BMP-2 at a physiological pH by the polymers according to the invention. On the other hand, sodium dextranmethylcarboxylate modified by ethyl phenylalaninate does not make it possible to obtain a clear BMP-2 solution.

What is claimed is:
1. A polysaccharide comprising carboxyl functional groups, at least one of which is substituted by a residue of a hydrophobic alcohol, and having a general formula I:

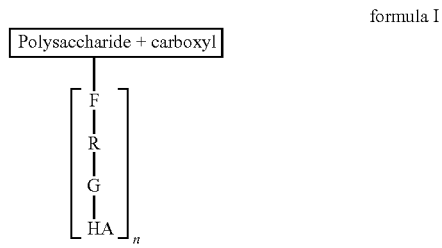

formula I in which
n represents a molar fraction of the carboxyl functions of the polysaccharide substituted by F-R-G-HA and is between 0.01 and 0.7,
said hydrophobic alcohol being grafted or bonded to the polysaccharide via a coupling arm R, said coupling arm being bonded to the polysaccharide via a function F, said function F resulting from the coupling between an amine function of the coupling arm R and a carboxyl function of the polysaccharide, and said coupling arm being bonded to the hydrophobic alcohol via a function G resulting from the coupling between a carboxyl function of the coupling arm and a function of the hydrophobic alcohol, the unsubstituted carboxyl functions of the polysaccharide being in the cationic carboxylate form, the cation being that of an alkali metal selected from the group consisting of Na⁺ and K⁺, F being an amide function, G being an ester function, R is an amino acid, HA being a residue of a hydrophobic alcohol, the hydrophobic alcohol being selected from the group consisting of fatty alcohols, alcohols composed of a saturated or unsaturated and branched or unbranched alkyl chain containing from 8 to 16 carbons, cholesterol derivatives, menthol derivatives, tocopherols and alcohols carrying an aryl group, the polysaccharide being selected from the group consisting of dextran, pullulan, alginate, hyaluronan, xylan, galacturonan, water-soluble cellulose, curdlan, inulin, glucan and mannan, said polysaccharide comprising carboxyl functional groups being amphiphilic at neutral pH.

2. The polysaccharide comprising carboxyl functional groups as claimed in claim 1, wherein the polysaccharide+carboxyl naturally carries carboxyl functional groups and is selected from the group consisting of alginate, hyaluronan and galacturonan.

3. The polysaccharide comprising carboxyl functional groups as claimed in claim 1, the polysaccharide+carboxyl being a synthetic polysaccharide obtained from a polysaccharide selected from the group consisting of dextran, pullulan, alginate, hyaluronan, xylan, galacturonan, water-soluble cellulose, curdlan, inulin, glucan and mannan, to which at least one acid function has been grafted, the polysaccharide+carboxyl having a general formula II:

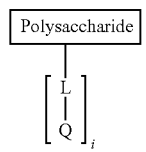

II

L being a function resulting from the coupling between the connecting arm Q and an —OH function of the polysaccharide, being either an ester, thioester, carbonate, carbamate or ether function, Q being a 1 to 18 carbon chain, wherein the chain (1) is optionally branched and/or unsaturated, (2) optionally includes one or more heteroatoms selected from the group consisting of O, N and S, and (3) has at least one acid function $CO_2H$.

4. The polysaccharide comprising carboxyl functional groups as claimed in claim 3, wherein the polysaccharide is dextran.

5. The polysaccharide comprising carboxyl functional groups as claimed in claim 3, wherein the polysaccharide is selected from the group consisting of pullulan, alginate, hyaluronan, xylan, galacturonan and a water-soluble cellulose.

6. The polysaccharide comprising carboxyl functional groups as claimed in claim 3, wherein the polysaccharide is curdlan.

7. The polysaccharide comprising carboxyl functional groups as claimed in claim 3, wherein the polysaccharide is inulin.

8. The polysaccharide comprising carboxyl functional groups as claimed in claim 3, wherein the polysaccharide is glucan.

9. The polysaccharide comprising carboxyl functional groups as claimed in claim 3, wherein the polysaccharide is mannan.

10. The polysaccharide comprising carboxyl functional groups as claimed in claim 3, wherein the L-Q group is selected from the group consisting of:

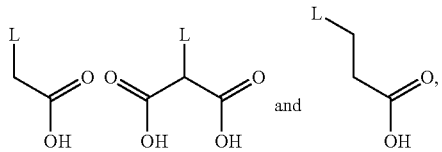

L being the function having the definition given in claim 3.

11. The polysaccharide comprising carboxyl functional groups as claimed in claim 1, wherein the amino acid is selected from the group consisting of α-amino acids.

12. The polysaccharide comprising carboxyl functional groups as claimed in claim 11, wherein the α-amino acids are natural amino acids selected from the group consisting of leucine, alanine, isoleucine, glycine, phenylalanine, tryptophan and valine.

13. The polysaccharide comprising carboxyl functional groups as claimed in claim 1, wherein the hydrophobic alcohol is selected from the group consisting of fatty alcohols.

14. The polysaccharide comprising carboxyl functional groups as claimed in claim 13, wherein the fatty alcohol is selected from the group consisting of myristyl alcohol, cetyl alcohol, stearyl alcohol, cetearyl alcohol, butyl alcohol, oleyl alcohol and lanolin.

15. The polysaccharide comprising carboxyl functional groups as claimed in claim 1, wherein the hydrophobic alcohol is selected from the group consisting of alcohols composed of a saturated or unsaturated and branched or unbranched alkyl chain containing from 8 to 16 carbons.

16. The polysaccharide comprising carboxyl functional groups as claimed in claim 1, wherein the hydrophobic alcohol is cholesterol.

17. The polysaccharide comprising carboxyl functional groups as claimed in claim 1, wherein the hydrophobic alcohol is menthol.

18. The polysaccharide comprising carboxyl functional groups as claimed in claim 1, wherein the hydrophobic alcohol is selected from the group consisting of tocopherols.

19. The polysaccharide comprising carboxyl functional groups as claimed in claim 1, wherein the hydrophobic alcohol is selected from the group consisting of alcohols carrying an aryl group.

20. The polysaccharide comprising carboxyl functional groups as claimed in claim 19, wherein the alcohol carrying an aryl group is selected from the group consisting of benzyl alcohol and phenethyl alcohol.

21. A pharmaceutical composition comprising the polysaccharide comprising carboxyl functional groups as claimed in claim 1 and at least one active principle.

22. The pharmaceutical composition as claimed in claim 21, which can be administered by an oral, nasal, vaginal or buccal route.

23. The pharmaceutical composition as claimed in claim 21, wherein the active principle is selected from the group consisting of proteins, glycoproteins, peptides and nonpeptide therapeutic molecules.

24. A method of preparation of a pharmaceutical composition comprising a polysaccharide comprising carboxyl functional groups and at least one active principle, comprising a step of adding the functionalized polysaccharide of claim 1 to a solution or a lyophilizate of the at least one active principle.

25. The method of preparation of the pharmaceutical composition according to claim 24, wherein the active principle is selected from the group consisting of proteins, glycoproteins, peptides and nonpeptide therapeutic molecules.

26. A method of preparation of a pharmaceutical composition comprising a polysaccharide comprising carboxyl functional groups and at least one active principle, which composition can be administered by an oral, nasal, vaginal or buccal route, comprising a step of adding the functionalized polysaccharide of claim 1 to a solution or a lyophilizate of the at least one active principle.

\* \* \* \* \*